(12) United States Patent
Van Landuyt

(10) Patent No.: US 6,379,332 B1
(45) Date of Patent: Apr. 30, 2002

(54) NEEDLE PROTECTOR DEVICES AND ASSEMBLIES

(75) Inventor: Christophe Van Landuyt, London (GB)

(73) Assignee: Smiths Industries public limited company, London (GB)

( * ) Notice: Subject to any disclaimer, the term of this patent is extended or adjusted under 35 U.S.C. 154(b) by 0 days.

(21) Appl. No.: 09/408,522

(22) Filed: Sep. 30, 1999

(30) Foreign Application Priority Data

Oct. 29, 1998 (GB) ............................................. 9823598

(51) Int. Cl.[7] ............................................. A61M 5/178
(52) U.S. Cl. ................................... 604/164.07; 604/263
(58) Field of Search ................................ 604/263–264, 604/272, 181, 187, 192, 194, 195, 197, 198, 200, 201, 205, 206, 236, 244, 158, 164.01, 164.07, 164.08, 164.09, 164.11, 167.01–167.02, 167.06, 168.01; 128/919

(56) References Cited

U.S. PATENT DOCUMENTS

| 5,300,043 A | 4/1994 | Devlin et al. |
| 5,300,045 A | 4/1994 | Plassche, Jr. |
| 5,458,658 A | 10/1995 | Sircom |
| 5,695,476 A | 12/1997 | Harris |
| 5,718,688 A | 2/1998 | Wozencroft |

FOREIGN PATENT DOCUMENTS

| EP | 0 747 083 | 12/1996 |
| EP | 0 875 261 | 11/1998 |
| GB | 2 324 734 | 11/1998 |

*Primary Examiner*—Brian L. Casler
*Assistant Examiner*—LoAn H. Thanh
(74) *Attorney, Agent, or Firm*—Connolly Bove Lodge & Hutz LLP

(57) ABSTRACT

A needle protector assembly for protecting a needle tip after it has been withdrawn from a catheter has a protective housing into which the needle is slid. A device at the patient end of the housing has two locking arms sprung outwardly away from one another, which engage projections on the hub of the catheter. A shutter plate and finger project inwardly from the locking arms and each has a catch that engages one another. The finger is sprung rearwardly away from the shutter plate but is held forwardly by a trigger lever engaging the side of the needle. When the needle is withdrawn into the housing, the trigger lever springs down allowing the finger to move rearwardly away from the shutter plate, thereby disengaging the catches. This allows the locking arms to spring outwardly and disengage the catheter hub, so that the assembly can be removed from the catheter.

12 Claims, 4 Drawing Sheets

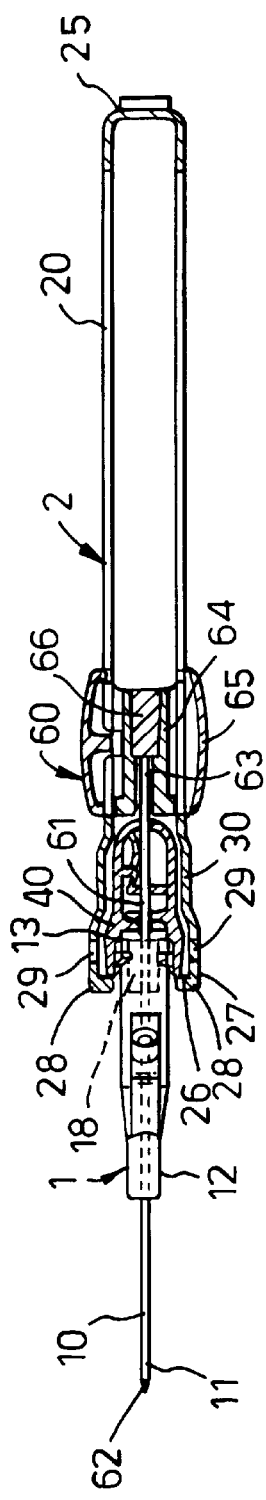
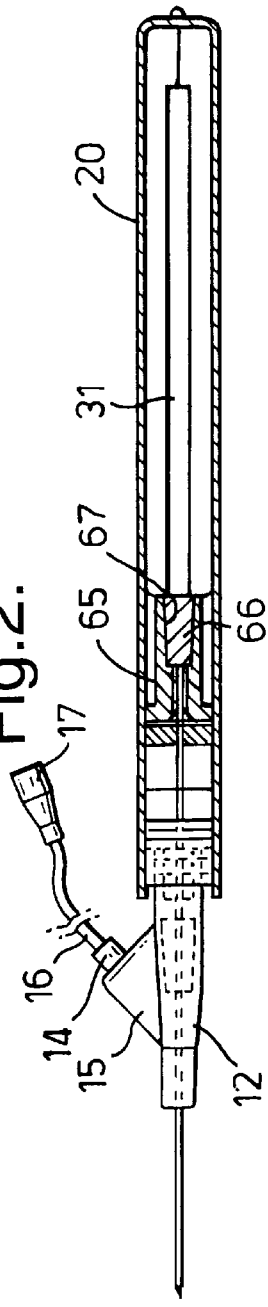
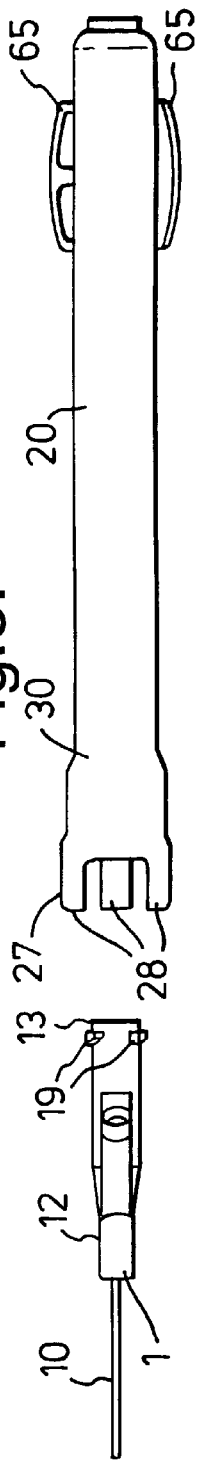

NEEDLE PROTECTOR DEVICES AND ASSEMBLIES

BACKGROUND OF THE INVENTION

This invention relates to needle protector devices and assemblies.

When a catheter is inserted in a vein or similar part of the body, this is often performed using a needle inserted within the catheter. The patient end of the needle is sharp and protrudes from the patient end of the catheter. The patient end of the assembly of the catheter on the needle is inserted in the vein and the needle is subsequently removed, leaving the catheter in position. The needle may be removed through a self-sealing port at the machine end of the catheter; a separate port is used to provide fluid access to the vein. Such an assembly is described, for example, in GB 2088215.

After the needle has been removed from the catheter, its patient end will carry traces of blood, which presents a potential contamination risk to the clinician and to people subsequently handling the needle. In order to protect the tip of the needle from contact after it has been withdrawn from the catheter, it has been proposed that the needle be withdrawn into a tubular protector after use, in the manner described in EP 545671 and EP 734272. In U.S. Pat. No. 4,978,344 there is described a tethered protective cap frictionally retained in a catheter hub so that it is pulled off the catheter and retained with the needle when the needle is pulled out of the catheter hub. Various other devices for protecting the tip of a needle when it is withdrawn from a catheter are described in, for example, U.S. Pat. No. 4,834,718, U.S. Pat No. 5,300,045, EP 799626, U.S. Pat. No. 4,944,725, EP 747083, U.S. Pat. No. 5,718,688 and GB2324734. These arrangements can suffer from various problems. For example, when the device is clamped onto the catheter hub by a member that engages the needle, so that removal of the needle releases the engagement with the hub, this can cause a high frictional force on the needle. Difficulties are also experienced in making practical devices that are effective but do not require close tolerances and costly manufacture.

BRIEF SUMMARY OF THE INVENTION

It is an object of the present invention to provide an improved catheter assembly.

According to one aspect of the present invention there is provided a needle protector device for protecting the tip of a needle after withdrawal of the needle from a catheter, the needle protector device including resilient means for locking with the hub of the catheter, first and second catch members engageable with one another to retain the locking means in engagement with the hub, trigger means arranged to engage the needle such that the trigger means is displaced from a first position when the needle projects into the catheter to a second position when the needle is withdrawn from the catheter, the trigger means being arranged to cooperate with the catch members such that the catch members are retained in engagement with one another when the trigger means is in the first position and can disengage from one another when the trigger means is in the second position.

The resilient means preferably includes two locking arms urged resiliently outwardly away from one another, the catch members being mounted with the arms. Each locking arm may have a hook portion towards one end arranged to engage a projection on the hub of the catheter when the arms are held inwardly. Each locking arm may have an inwardly-projecting member, the catch members being mounted with respective ones of the inwardly-projecting members. One of the inwardly-projecting members preferably has an aperture through which the needle projects when the needle extends in the catheter. The needle protector device is preferably arranged to prevent the needle being extended after it has been withdrawn. The aperture on the one inwardly-projecting member may be displaced out of alignment with the needle when the needle is withdrawn from the catheter. One of the inwardly-projecting members may be urged resiliently away from the other and be held against the other by the trigger means. The trigger means preferably includes a generally longitudinally-extending member urged resiliently laterally against the side of the needle. The needle protector is preferably made as a one-piece plastics molding.

According to another aspect of the present invention there is provided a needle assembly for use with a catheter, the needle assembly including a needle shaft, an elongate protective housing, a slider mounted with the machine end of the needle shaft and slidable along the housing from a first position in which the patient end of the shaft protrudes from the housing to a second position in which the patient end of the shaft is protected within the housing, and a needle protector device according to the above one aspect of the invention located at the patient end of the housing, such that the needle protector device retains the needle assembly with the catheter when the needle extends within the catheter and disengages the needle assembly from the catheter when the needle is withdrawn into the protective housing.

A venous catheter assembly in accordance with the present invention, will now be described, by way of example, with reference to the accompanying drawings.

BRIEF DESCRIPTION OF THE DRAWINGS

FIG. 1 is a sectional plan view of the assembly with the needle assembly connected with the catheter;

FIG. 2 is a sectional side elevation view of the assembly of FIG. 1;

FIG. 5 is a plan view of the assembly with the needle assembly separated from the catheter;

DETAILED DESCRIPTION OF THE PREFERRED EMBODIMENTS

Figure 3:
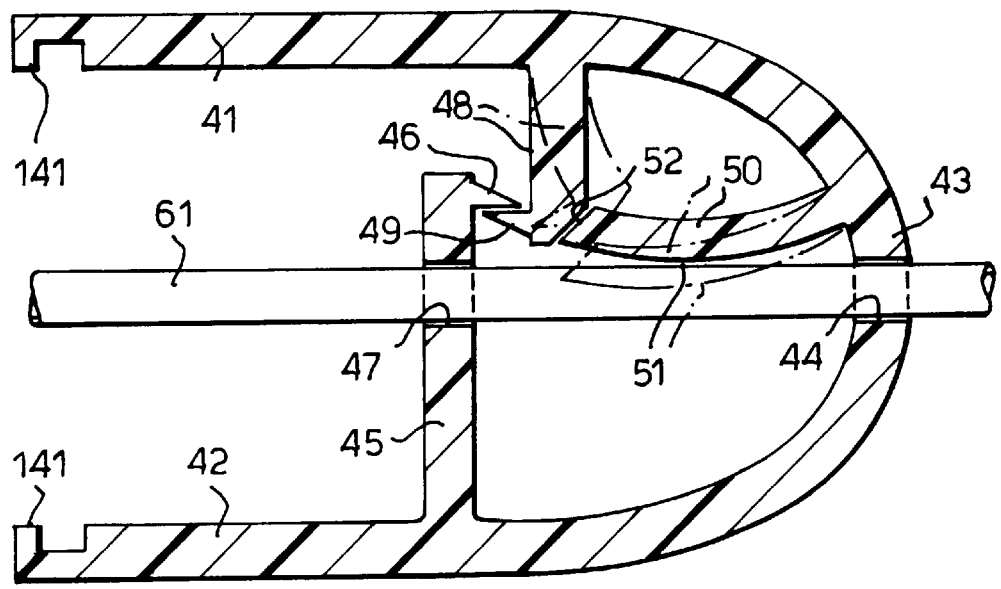
FIG. 3 is an enlarged sectional plan view of a part of the assembly in a locked state.

With reference to FIGS. 1 to 3, the assembly comprises a catheter 1 and a needle assembly 2. The needle assembly 2 is used to introduce the catheter 1 into a vein and is subsequently removed and discarded.

The catheter 1 is a conventional venous catheter, such as sold by SIMS Portex Limited under the trade mark Y-Can. The catheter 1 has a flexible tubular shaft 10 with an open patient end 11. The machine end of the shaft 10 is secured in a rigid, plastics hub 12, which has a machine end port 13 aligned axially with the shaft, and a side port 14 on a wing member 15. A small-bore flexible tube 16 is bonded to the side port 14 and extends away from the hub at an angle of about 45 degrees. The tube 16 is terminated by a connector 17. Both the bore in the tube 16 and the port 13 communicate with the passage through the catheter shaft 10, but the port 13 contains a self-sealing septum 18, which seals closed after withdrawal of the needle. Externally, the hub 12 has two wedge-shape projections 19 arranged diametrically opposite one another around the machine end port 13, which provide a screw-thread for securing a cap, or other luer-compatible device, to the port after removal of the needle assembly. Instead of these projections, alternative surface formations could be provided.

The needle assembly 2 comprises an outer elongate protective housing 20, a needle protector device 40 located at the patient end of the housing, and a needle member 60 slidable along the housing.

The housing 20 is molded from a rigid, transparent plastics material, such as modified styrene and is about 10 mm long and about 10 mm square in section along most of its length. The rear, machine end 25 of the housing is closed. The forward, patient end 26 of the housing 20 is open. At its open end 26, the housing 20 is increased in width along two regions. In the first region 27, at the forward end of the housing, it is divided into three axially-extending prongs 28 equally spaced around the housing, the width of the housing across the prongs being about 14 mm. Each prong 28 has a small aperture 29 through it for assembly purposes. This forward region 27 connects with an adjacent region 30 where the housing 20 is continuous around its periphery and which has a width of about 12 mm. The height of the housing 20 is the same along its entire length. The housing 20 has two slots 31 extending axially on opposite side and terminating just short of the forward and rear ends of the housing.

The needle protector device 40 is located in the enlarged regions 27 and 30 at the forward end of the housing 20 and is molded as one piece from a stiff, resilient plastics material, such as polypropylene. The needle protector device 40 is a relatively loose fit within the housing 20 but the fit is such as to ensure that it cannot be slid rearwardly along the housing. The needle protector device 40 has two locking arms 41 and 42 connected at their rear end by a curved spring portion 43, which has a central aperture 44. At their forward ends, the arms 41 and 42 each have an inwardly-directed locking hook 141 shaped to engage the projections 19 on the catheter hub 12. About half way along its length, the lower arm 42 has a shutter plate 45 projecting laterally inwardly towards the other arm. The shutter plate 45 has a rearwardly-projecting catch 46 at its free end and an aperture 47 located centrally. The upper arm 41 has an inwardly-projecting finger 48 with a forwardly-projecting catch 49. The finger 48 is urged laterally by its resilience so that its natural position is curved rearwardly away from the shutter plate 45, as shown by the broken lines in FIG. 3, with the catch 49 disengaged from the catch 46. The needle protector device 40 also includes a trigger lever 50 projecting from the spring portion 43 extending generally longitudinally, substantially parallel to the upper arm 41. The trigger lever 50 is curved upwardly along its length so that its lower side 51 presents a convex profile, the free end 52 of the trigger lever 50 being bevelled. The trigger lever 50 can be deformed up to the first position, shown by the solid lines in FIG. 3, so that its free end 52 engages the right-hand side of the finger 48 and holds it forwardly with the catch 49 engaging under the catch 46 on the shutter plate 45. The second, natural position of the trigger lever 50, however, is shown by the broken lines in FIG. 3 where it inclines downwardly and its free end 52 is displaced away from the finger 48.

The needle member 60 has a hollow metal needle shaft 61 with a sharply pointed, chamfered patient end 62, the length of the needle member being such that its patient end just projects beyond the patient end 11 of the catheter shaft 10. The rear machine end 63 of the shaft 61 is mounted in the central body portion 64 of a slider 65 molded from a transparent plastics material, such as ABS. The rear end 63 of the needle shaft 61 abuts the forward end of a hydrophobic vent plug 66 secured in an open recess 67 at the rear end of the body portion 64. The body portion 64 of the slider 65 is a loose fit within the housing 20 so that it can be slid freely along its length. The slider 65 projects laterally outwardly from opposite sides of the body portion 64, through the slots 31 so that it can be accessed externally.

The catheter assembly is supplied in the condition shown in FIGS. 1 to 3. The slider 65 of the needle member 60 is located at the forward end of the housing 20 and the needle shaft 61 extends along the bore of the shaft 10 of the catheter 1, with its patient end 62 just projecting from the patient end 11 of the catheter. The needle shaft 61 projects through the needle protector device 40 and, more particularly, it projects through the aperture 44 in the curved portion 43, under the lower side 51 of the trigger lever 50 and through the aperture 47 in the shutter plate 45. The trigger lever 50 is urged laterally, downwardly against the needle shaft 61 by its resilience. The needle shaft 61 holds up the trigger lever 50 so that its free end 52 engages the finger 48 and holds its catch 49 in engagement with the catch 46 on the shutter plate 45. With the two catches 46 and 49 engaged in this way, the two arms 41 and 42 are held towards one another, against their resilience and that of the curved portion 43, with the hooks 141 on the arms engaging the projections 19 on the catheter hub 12. The resilient force tending to separate the two arms 41 and 42 is applied to the catches 46 and 49, not to the needle 61, so the only impediment to movement of the needle is the friction with the trigger lever 50, which can be low.

Figure 6:
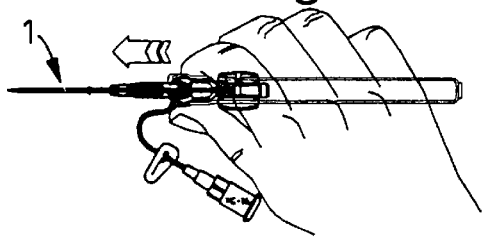
FIGS. 6 to 10 are plan views illustrating different steps in use of the assembly.

In use, the assembly is gripped at the forward end of the housing 20 and the forward end 62 of the needle 60 and catheter 10 is pushed into a vein, in the usual way, as shown in FIG. 6. When venepuncture has been achieved, blood flows along the bore of the needle shaft 61, air in the needle being expelled through the hydrophobic vent 66. When blood reaches this vent 66, the hydrophobic material absorbs the blood and turns red, which color change is visible by the user through the slider 65 and housing 20. When the vent 66 is wetted, it seals to prevent escape of blood.

Figure 4:
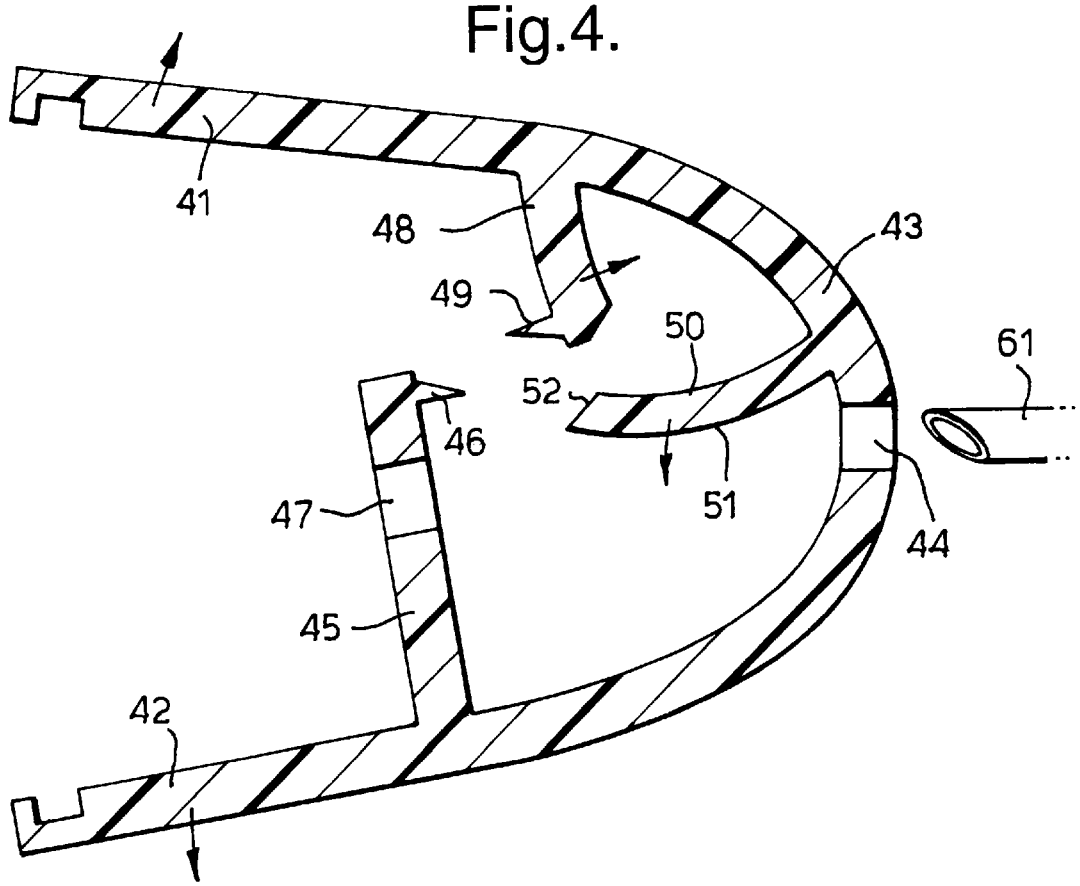
FIG. 4 is an enlarged sectional plan view of the part in FIG. 3 in an unlocked state.
Figure 7:
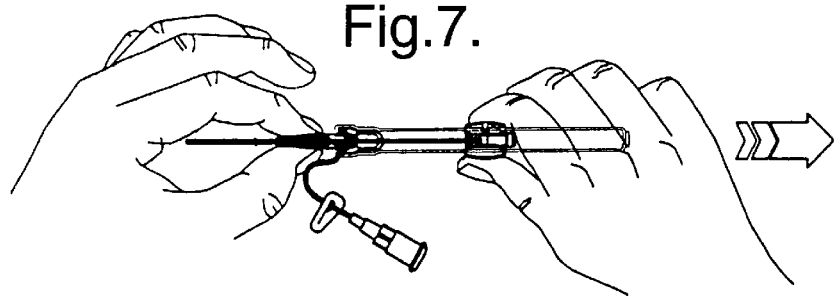
Figure 8:
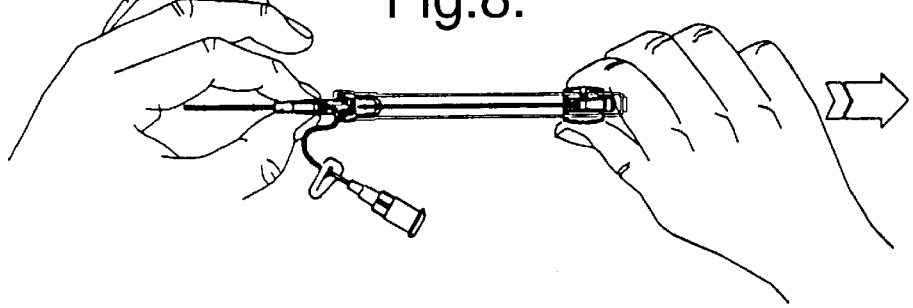
Figure 9:
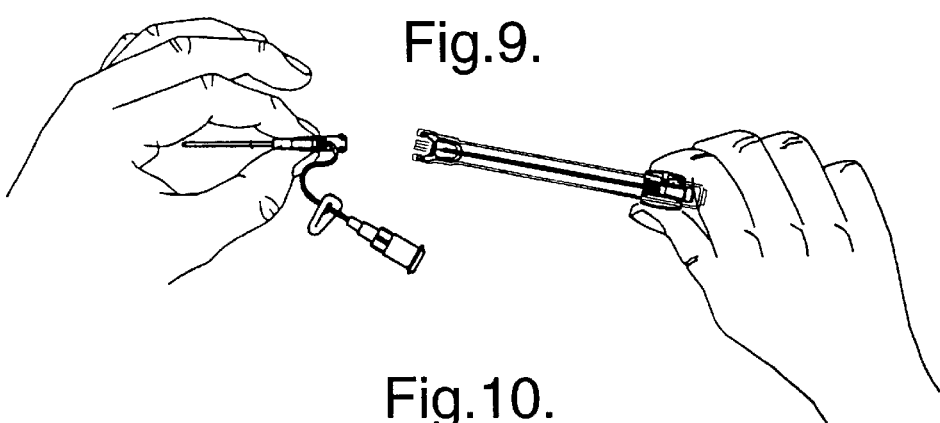
Figure 10:
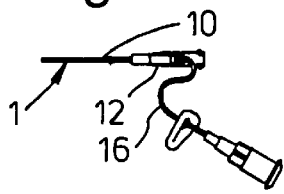

The user then holds the hub 12 of the catheter 1 with one hand and holds the slider 65 between the finger and thumb of the other hand. He pulls the slider 65 rearwardly along the housing 20 so that the needle shaft 61 is withdrawn from the shaft 10 of the catheter 1, as shown in FIG. 7. The housing 20 remains securely attached to the catheter hub 12 during this process. As the tip 62 of the needle 60 is pulled out of the hub 12 of the catheter 1, its self-sealing septum 18 prevents flow of blood out of the hub. When the slider 65 is pulled back to its full extent along the housing 20, as shown in FIG. 8, the patient end of the needle is withdrawn through the aperture 47 and then disengages from the trigger lever 50. When the trigger lever 50 is disengaged by the needle shaft 61, it springs down to its second position so that its free end moves away from the catch finger 48 allowing this to deflect, to the right, away from the shutter 45, as shown in FIG. 4. When the catch 49 clears the catch 46, the two arms 41 and 42 spring out under their natural resilience so that their hooks 141 disengage the projections 19 on the catheter hub 12. Once the hooks 141 are disengaged from the projections 19 on the catheter hub 12 the needle assembly 2 is unlocked from the catheter 1, as shown in FIGS. 5 and 9. The catheter 1 remains in position in the patient, as shown in FIG. 10. Its hub 12 is preferably closed with a cap screw threaded onto the projections 19, and the tube 16 is used to make access to the vein.

The patient end 62 of the needle 60 is located in the protective housing 20 rearwardly of the needle protector device 40. Because the shutter plate 45 is deflected down with the arm 42, the aperture 47 moves out of alignment with the needle 60, thereby preventing the needle being subsequently extended and locking it safely within the housing 20. The housing 20 cannot be removed from the catheter 1 until the needle 60 is fully enclosed within the housing, so there is no risk of accidental needle prick and contamination.

Figure 11:
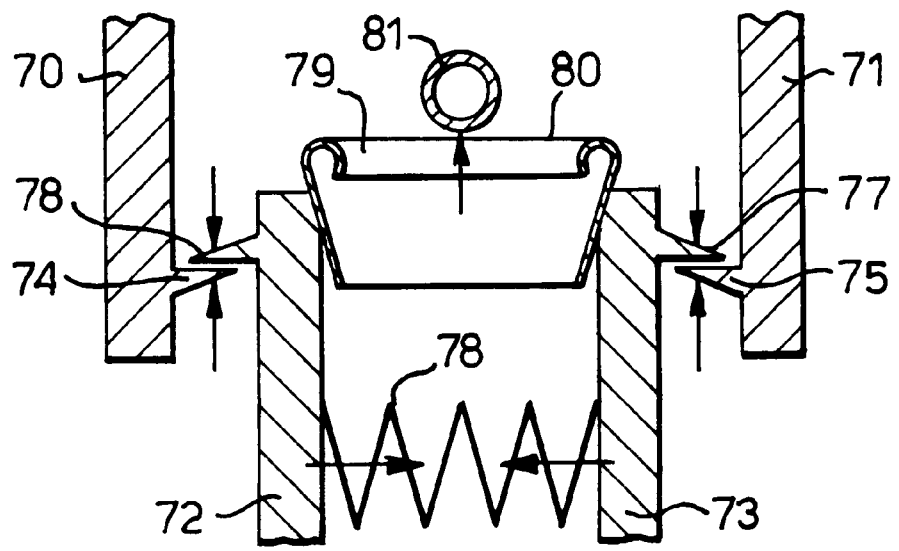
FIG. 11 is a sectional elevation view of a part of an alternative needle protector device.

Various modifications are possible. For example, the catch need not be provided on the shutter plate, or other component preventing extension of the needle, it could be provided on a separate component. One alternative arrangement is shown in FIG. 11. This has a pair of fingers 70 and 71 extending down from one locking arm (not shown) and a pair of fingers 72 and 73 extending up from the other locking arm. The upper pair of fingers 70 and 71 are fixed and have inwardly-projecting catches 74 and 75. The lower pair of fingers 72 and 73 extends between the upper pair of fingers 70 and 71 and have outwardly-projecting catches 76 and 77 arranged to engage the catches 74 and 75 on the upper pair of fingers. The lower fingers 72 and 73 are urged together by a spring 78 so that its catches 75 and 77 are urged away from the catches 74 and 75 on the upper fingers 70 and 71. The lower fingers 72 and 73 are kept apart, so that the catches 74 and 76, 75 and 77 engage, by trigger means in the form of a wedge 79 located between the upper end of the lower fingers. The upper surface 80 of the wedge 79 engages the underside of the needle 81, which holds it down in a first position between the lower fingers. When the needle 81 is withdrawn, the spring 78 is free to pull the two lower fingers 72 and 73 together, since the wedge 79 is now free to be pushed up to a second position. As the two lower fingers 72 and 73 move together, the catches 76 and 77, 74 and 75 clear one another, enabling the two locking arms to spring apart and release the lock with the catheter hub.

Figure 12:
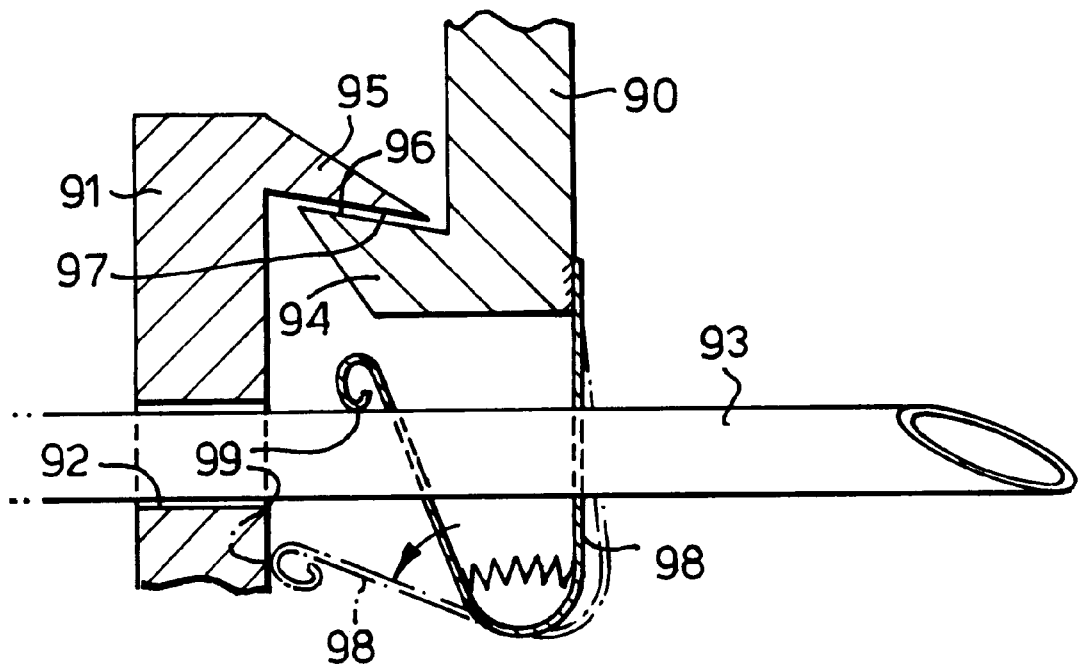
FIG. 12 is a sectional elevation view of a part of another alternative needle protector device.

In the arrangement shown in FIG. 12, the two locking arms have respective fingers 90 and 91 extending towards one another, the upper finger 90 being fixed and the lower finger 91 being resiliently biased anticlockwise away from the upper finger. The lower finger 91 has an aperture 92 through which the needle 93 extends freely. The two fingers 90 and 91 each have a catch 94 and 95, which have inclined engaging surfaces 96 and 97 arranged such that the force required to disengage the lower finger 91 is greater than the resilient bias force urging it anticlockwise. The upper finger 90 has trigger means in the form of a curved spring element 98 extending down from the finger and being looped above the needle 93 with its free end 99 bearing down on its upper surface. The resilience of the spring element 98 is such that its free end 99 is urged down. The dimensions of the spring element 98 are such that when the needle 93 is withdrawn, the free end 99 of the spring deflects down to a second position shown by the broken lines where it engages the right-hand side of the lower finger 91, thereby applying a force to the finger tending to rotate it anticlockwise. The force applied by the spring element 98 combined with the inherent resilience of the lower finger 91 is sufficient to disengage the two catches from one another and thereby allow the two locking arms to separate.

It will be appreciated that the invention is not confined to venous catheter assemblies but could be used with other catheter assemblies where a needle or similar sharp device extends along the catheter for introducing the catheter.

What I claim is:

1. A needle protector device for protecting a tip of a needle, wherein the needle protector device comprises: resilient locking means for locking with a hub of a catheter; first and second catch members engageable with one another to retain said locking means in engagement with said hub; trigger means, said trigger means being arranged to engage a needle such that said trigger means is displaced from a first position when said needle projects into said catheter to a second position when said needle is withdrawn from said catheter, and wherein said trigger means is arranged to cooperate with said catch members such that said catch members are retained in engagement with one another when said trigger means is in said first position and can disengage from one another when said trigger means is in said second position.

2. A needle protector device according to claim 1, wherein said resilient locking means includes two locking arms urged resiliently outwardly away from one another, and wherein said catch members are mounted with said arms.

3. A needle protector device according to claim 2, wherein each said locking arm has an inwardly-projecting member, and wherein said catch members are mounted with respective ones of said inwardly-projecting members.

4. A needle protector device according to claim 3, wherein one of said inwardly-projecting members has an aperture through which said needle projects when said needle extends in said catheter.

5. A needle protector device according to claim 4, wherein said aperture on said one inwardly-projecting member is displaced out of alignment with said needle when said needle is withdrawn from said catheter.

6. A needle protector device according to claim 3, wherein one of said inwardly-projecting members is urged resiliently laterally away from said other member and is held against said other member by said trigger means.

7. A needle protector device according to claim 2, wherein each said locking arm has a hook projection towards one end, and wherein said hook portions are arranged to engage a projection on said hub of said catheter when said arms are held inwardly.

8. A needle protector device according to claim 1, wherein said needle protector device is arranged to prevent said needle being extended after it has been withdrawn.

9. A needle protector according to claim 1, wherein said trigger means includes a generally longitudinally-extending member urged resiliently laterally against a side of said needle.

10. A needle protector according to claim 1, wherein said needle protector is a one-piece plastics molding.

11. A needle protector device for protecting a tip of a needle, wherein the needle protector device comprises: two resiliently mounted locking arms arranged to lock with a hub of a catheter; a shutter plate projecting inwardly from one of said arms; a finger projecting inwardly from the other of said arms, said fingers being urged resiliently laterally away from said shutter plate; a first catch member on said shutter plate; a second catch member on said finger engageable with said first catch member to retain said locking arms in engagement with said hub; a trigger lever, said trigger lever extending generally longitudinally and bearing resiliently on a side of said needle, with one end of said trigger lever engaging said finger and holding it against said shutter plate so that said two catches engage one another when said needle projects into said catheter, and wherein said trigger lever moves away from said finger when said needle is withdrawn, thereby allowing the finger to move laterally away from said shutter plate and allowing said two catches to disengage one another so that said two locking arms can move apart and disengage from said hub.

12. A needle assembly for use with a catheter, said needle assembly comprising: a needle shaft; and elongate protective housing; a slider mounted with a machine end of said needle shaft and slidable along said housing from a first position in which a patient end of said shaft protrudes from said housing into said catheter to a second position in which the patient end of said shaft is protected within said housing; and a needle protector device for protecting a patient end of said needle shaft, wherein said needle protector device comprises: resilient locking means for locking with a hub of said catheter; first and second catch members engageable with one another to retain said locking means in engagement with said hub; trigger means, said trigger means being arranged to engage said needle shaft such that said trigger means is displaced from a first position when said needle projects into said catheter to a second position when said needle is withdrawn from said catheter into said housing, and wherein said trigger means is arranged to cooperate with said catch members such that such catch members are retained in engagement with one another when said trigger means is in said first position and can disengage from one another when said trigger means is in said second position, such that said needle protector device retains said catheter with said needle assembly when said needle extends within said catheter and disengages said catheter from said needle assembly when said needle is withdrawn into said protective housing.

* * * * *